United States Patent
Kreuter et al.

(10) Patent No.: US 7,074,436 B2
(45) Date of Patent: Jul. 11, 2006

(54) METHOD FOR THE PRODUCTION OF PHYLLANTHUS EXTRACTS

(75) Inventors: Matthias-Heinrich Kreuter, Walenstadt (DE); Hildebert K. M. Wagner, Breitbrunn a. Chiemsee (DE); Gerolf Tittel, Gräfelfing (DE)

(73) Assignee: Phytrix, Inc., Munich (DE)

( * ) Notice: Subject to any disclaimer, the term of this patent is extended or adjusted under 35 U.S.C. 154(b) by 236 days.

(21) Appl. No.: 10/398,380

(22) PCT Filed: Oct. 5, 2001

(86) PCT No.: PCT/EP01/11526

§ 371 (c)(1),
(2), (4) Date: Sep. 4, 2003

(87) PCT Pub. No.: WO02/30436

PCT Pub. Date: Apr. 18, 2002

(65) Prior Publication Data

US 2004/0033275 A1    Feb. 19, 2004

(30) Foreign Application Priority Data

Oct. 6, 2000 (EP) .................................. 00121852
Jan. 15, 2001 (EP) .................................. 00100825

(51) Int. Cl.
*A61K 35/78* (2006.01)
*A61K 31/00* (2006.01)

(52) U.S. Cl. .................................. 424/725; 424/195.18

(58) Field of Classification Search ................ 424/725, 424/195.18

See application file for complete search history.

(56) References Cited

U.S. PATENT DOCUMENTS

| | | | |
|---|---|---|---|
| 3,098,849 A * | 7/1963 | Mainil | 424/773 |
| 3,272,796 A * | 9/1966 | Mainil | 546/1 |
| 4,388,457 A | 6/1983 | Pettit | 536/4.1 |
| 4,673,575 A | 6/1987 | Venkateswaran et al. | 424/195.1 |
| 4,937,074 A | 6/1990 | Venkateswaran et al. | 424/195.1 |
| 5,529,778 A | 6/1996 | Rohatgi | 424/195.1 |
| 5,571,441 A | 11/1996 | Andon et al. | 252/1 |
| 5,648,089 A | 7/1997 | Shawkat | 424/434 |
| 5,854,233 A | 12/1998 | McLean | 514/211 |
| 6,136,316 A | 10/2000 | Mehrotra et al. | 424/195.1 |
| 6,586,015 B1 | 7/2003 | Gebhardt et al. | 424/725 |
| 2004/0028754 A1 | 2/2004 | Von Keudell et al. | 424/725 |
| 2004/0161477 A1 | 8/2004 | Wagner et al. | 424/725 |

FOREIGN PATENT DOCUMENTS

| | | |
|---|---|---|
| EP | 0061161 | 9/2000 |
| WO | 8909059 | 10/1989 |
| WO | 9004968 | 5/1990 |
| WO | WO 00/56347 * | 9/2000 |

OTHER PUBLICATIONS

Database BIOSIS 'Online! Bioscience Information Service, Philadelphia, PA, US; 1993 Munshi Anupama et al: "Evaluation of anti-hepadnavirus activity of *Phyllanthus amarus* and *Phyllanthus maderaspatensis* in duck hepatitis B virus carrier Pekin ducks." Database accession No. PREV199497070792 XP002189216 Zusammenfassung & Journal of Medical Virology, Bd. 41, Nr.4, 1993, Seiten 275-281.

Database BIOSIS 'Online! Biosciences Information Service, Philadelphia, PA, US; 1991 Mehrotra R et al: "In-Vitro Effect of *Phyllanthus-Amarus* on Hepatitis B Virus" Database accession No. PREV199191116067 XP002189217 Zusammenfassung & Indian Journal of Medical Research Section A, Bd. 93, Nr. Mar., 1991, Seiten 71-73.

International Search Report, dated Feb. 5, 2002.

Thyagarajan et al., "Effect of *Phyllanthus Amarus* on Chronic Carriers of Hepatitis B Virus," *The Lancet*, Oct. 1, 1988, pp. 764-766.

(Continued)

Primary Examiner—Christopher R. Tate
(74) Attorney, Agent, or Firm—Baker Botts L.L.P.

(57) ABSTRACT

A method for the production of an extract of *Phyllanthus* wherein (a) *Phyllanthus*components are extracted with an ethanol/water mixture of 5–85% m/m to which a heavy-metal chelator is added at a concentration of 0.001–3% m/m; (b) the primary extract obtained in step (a) is contacted and concentrated with (ba) Indian Sterculia gum at a final concentration of 0.5–5.0% mm relative to the sum of the extractive substances or (bb) one or more polymers and impendable and/or soluble substance(s); and (c) the concentrated extract obtained in step (b) is dried. The method according to the invention leads to particularly high yield of pharmaceutically effective plant ingredients and is thus of particular interest for therapeutic applications. In a preferred embodiment of the invention the method according to the invention includes a filtration step of the primary extract. It is further preferred that a lipoid is added during the extraction method. The *Phyllanthus Phyllanthus amarus* is preferred. Moreover, the invention relates to pharmaceutical compositions containing the extracts obtained by the method of the invention.

27 Claims, No Drawings

OTHER PUBLICATIONS

Venkateswaran et al., "Effects of an extract from *Phyllanthus niruri* on hepatitis B and woodchuck hepatitis viruses: *In vitro* and *vivo* studies," *Proc. Natl. Acad. Sci. USA*, vol. 84, pp. 274-278, Jan. 1987.

Thyagarajan et al., "*In vitro* inactivation of HBsAg by *Eclipta alba* Hassk and *Phyllanthus niruri* Linn," *Indian J Med Res* 76 (Suppl), pp. 124-130, Dec. 1982.

Syamasundar et al., "Antihepatotoxic principles of *Phyllanthus niruri* herbs," *J Ethnopharmacol* 14(1):41-4, Sep. 1985. Abstract from National Library of Medicine: IGM Full Record Screen.

del Barrio Alonso et al., "The in-vitro inactivation of HBsAg by extracts of plants in the genus Phyllanthus," *Rev Cubana Med Trop.*, 47(2):127-130, 1995. Abstract from National Library of Medicine: IGM Full Record Screen.

Doshi et al., "A two-stage clinical trial of *Phyllanthus amarus* in hepatitis B carriers: failure to eradicate the surface antigen," *Indian J Gastroenterol.*, 13(1):7-8, 1994. Abstract from National Library of Medicine: IGM Full Record Screen.

el-Mekkway et al., "Inhibitory effects of Egyptian folk medicines on human immunodeficiency virus (HIV) reverse transcriptase," *Chem Pharm Bull (Tokyo)*, 43(4):641-8, 1995. Abstract from National Library of Medicine: IGM Full Record Screen.

Wang et al., "Herbs of the genus of Phyllanthus in the treatment of chronic hepatitis B: observations with three preparations from different geographic sites," *J Lab Clin Med.*, 126(4):350-2, Oct. 1995. Abstract from National Library of Medicine: IGM Full Record Screen.

Wang et al., "Efficacy of Phyllanthus spp. in treating patients with chronic hepatitis B," *Chung Kuo Chung Yao Tsa Chih.*, 19(12):750-1, 764, 1994. Abstract from National Library of Medicine: IGM Full Record Screen.

Powis et al., "High-performance liquid chromatographic assay for the antitumor glycoside phyllanthoside and its stability in plasma of several species,"*J Chromatogr*, 342(1):129-34, Jul. 12, 1985. Abstract from National Library of Medicine; IGM Full Record Screen.

Zhou Shiwen Xu Chuanfu et al., "Mechanism of protective action of *Phyllanthus urinaria* L. against injuries of liver cells," *Zhongguo Zhongyao Zazhi*, 22(2):109-111,129; 1997. Abstract from Datenbank BIOSIS bei STN:AN 1997:211857 BIOSIS, DN PREV 199799511060.

Asha et al., "Preliminary evaluation of the antihepatotoxic activity of *Phyllanthus kozhikodianus, P. maderaspatensis* and Solanum indicum," *Fitoterapia*, 69(3):255-259, 1998. Abstract from Database Biosis 'Online! Biosciences Information Service, Philadelphia, PA, US; 1998.

Jeena et al., "Effect of Emblica officinalis, *Phyllanthus amarus* and *Picrorrhiza kurroa* on N-nitrosodiethylamine induced hepatocarcinogenesis," *Cancer Letters*, 136(1):11-16, 1999. Abstract from Database Biosis 'Online! Biosciences Information Service, Philadelphia, PA, US; Feb. 8, 1999.

Hu et al., "Process for preparing Gynostemma pentaphylla throat-moistening tablets—useful for treating bronchitis, asthma, and cancer." Abstract from Chemical Patents Index, Documentation Abstracts Journal Derwent Publications, London: Mar. 19, 1999, Nr.99-081999/08 zu: CN 1194857-A.

Nippon Mektron KK (assignee), "Lipid metabolism improving and liver disturbance inhibitory agents—comprise organic solvent or water extract of Euphorbiaceae family, *Phyllanthus niruri*." Abstract from Chemical Patents Index, Documentation Abstracts Journal Derwent Publications, London: Dec. 19, 1997,Nr.97-508797/47 zu: JP 09241176 A.

Hou et al., "SOD prepared from *phyllanthus emblica* used as health food additive." Abstract from Chemical Patents Index, Documentation Abstracts Journal Derwent Publications, London: Dec. 12, 1997,Nr.97-490386/46 zu: CN 1121783 A.

Mikimoto Seiyaku KK (assignee), "Cosmetic material having good skin-moisturising effect—consists of compounded mixt. of cholesteric liq. crystal and one or more of e.g. Piper longum, P. chaba etc." Abstract from Chemical Patents Index, Documentation Abstracts Journal Derwent Publications, London: Sep. 29, 1995,Nr.95-252224/33 zu: JP 07157420 A.

Mikimoto Seiyaku KK (assignee), "Antioxidants used in lotions, creams and emulsions—contain solvent extract from e.g. nigella savia, munronia pumila or borrelia hispida." Abstract from Chemical Patents Index, Documentation Abstracts Journal Derwent Publications, London:Sep. 8, 1995,Nr.95-228590/30 zu: JP 07138126 A.

Cao et al., "Antioxidant for cosmetic products." Abstract from Chemical Patents Index, Documentation Abstracts Journal Derwent Publications, London: Sep. 8, 1995,Nr.95-224715/30 zu: CN 1086532 A.

Xiao et al., "Extraction of *Phyllanthus emblica* polysaccharides (PePS) and its scavenging effect on oxygen radical," *Zhongguo Yaoxue Zazhi (Beijing)*, 33(5):279-281, 1998. Abstract from Chemical Abstracts 130:452b.

Joy et al., "Inhibition of *Phyllanthus amarus* of hepatocarcinogenesis induced by N-nitrosodiethylamine," *Journal of Clinical Biochemistry and Nutrition*, 24(3):133-139, 1998. Abstract from Datenbank BIOSIS bei STN:AN 1999:13953 BIOSIS, DN PREV 199900013953.

Potturi et al., "Protective effect of *Phyllanthus fratemus* against thioacetamide-induced mitochondrial dysfunction," *Journal of Clinical Biochemistry and Nutrition*, 22(2):113-123, 1997. Abstract from Datenbank BIOSIS bei STN:AN 1997-4431146 BIOSIS, DN PREV 199799742349.

Ihantola-Vormisto et al., Plant Medica (Dec. 1997), 63(6): 518-524. Anti-inflammatory activity of extracts from leaves of *Phyllanthus emblica*.

Xia Quan et al., "Ethnopharmacology of *Phyllanthus emblica* L.," *Zhongguo Zhongyao Zazhi*, 22(9):515-518, 525, 574; 1997. Abstract from Database Biosis 'Online! Biosciences Information Service, Philadelphia, PA, US.

Suresh et al., "Augmentation of murine natural killer cell and antibody dependent cellular cytotoxicity activities by *Phyllanthus emblica*, a new immunomodulator," *J Ethnopharmacol*, 44(1):55-60, Aug. 1994. Abstract from Database Biosis 'Online! Biosciences Information Service, Philadelphia, PA, US.

Calixto et al., "Antispasmodic effects of an alkaloid extracted from *Phyllanthus sellowianus*: a comparative study with papaverine," *Braz J Med Biol Res*, 17(3-4):313-21, 1984. Abstract from National Library of Medicine: IGM Full Record Screen.

Shanmugasundaram et al., "Anna Pavala Sindhooram—an antiatherosclerotic Indian drug," *J Ethnopharmacol*, 7(3):247-65, May 1983. Abstract from National Library of Medicine: IGM Full Record Screen.

Unander et al., "Uses and bioassays in *Phyllanthus* (Euphorbiaceae): a compilation II. The subgenus *Phyllanthus*," *Journal of Ethnopharmacology*, 34: 97-133, 1991.

Lee et al., "Regulation of Hepatitis B Virus Replication and Gene Expression by an Extract from *Phyllanthus Niruri*," AASLD ABSTRACTS p. 117A, (#241) *Hepatology*, vol. 18, No. 4, Pt. 2, 1993.

Chintalwar et al., "An immunologically active arabinogalactan from *Tinospora cordifolia*," *Phytochemistry* 52:1089-1093, 1999.

Matthée et al., "HIV Reverse Transcriptase Inhibitors of Natural Origin," *Planta Medica* 65:493-506. 1999.

*Neueste Literatur zu Polysacchariden mit Immunstimulierender Wirkung*, Chapters in Immunomodulatory Agents from Plants, by H. Wagner (editor), Birkhäuser Verlag Basel-Boston-Berlin, 1999, pp. 1-39; 89-104; 161-201; 203-221; 325-356.

Thabrew et al., J of Ethnopharmacology (1991), 33(1-2): 63-66. Immunomodulatory activity of three Sri-Lankan medicinal plants used in hepatic disorders.

Paya et al., Phytotherapy Research (1996), 10: 228-232. Inhibitory effects of various extracts of Argentine plant species on free-radical-mediated reactions and human neutrophil functions.

Hagers Handbuch der Pharmazeutischen Praxis, 5. Ed., Folgeband 3, Drogen L-Z, Springer Verlag, Heidelberg 1998, pp. 338-352.

Ihantola-Vormisto et al., Plant Medica (Dec. 1997), 63(6): 518-524. Anti-inflammatory activity of extracts from leaves of *Phyllanthus* emblica.

S. Jayaram et a., Indian J. Virol. Vo. 13, No. 1, pp. 59-64 Efficacy of *Phyllanthus Amarus* Treatment in Acute Viral Hepatitis A,B and Non A Non B: An Open Clinical Trial (Jan. 1997).

P. Ferenci Gut 1993; supplement: S69-S73 Historical Treatment of Chronic-Hepatitis B and Chronic Hepatitis C.

Steven P. Lawrence, M.D., Advances in Internal Medicine, vol. 45 2000 Mosby, Inc., Advances in the treatment of hepatitis C.

Database BIOSIS Online! Bioscience Information Service, Philadelphia, PA, US; 1999 Houghton P. J. et al., "The anti-HIV activity of an aqueous extract and polyphenolic compounds of *Phyllanthus amarus*", Database accession No. PREV199900538759 XP-002191772, abstract & Journal of Pharmacy and Pharmacology, vol. 51, No. SUPPL., 1999, pg. 100 136th British Pharmaceutical Conference; Cardiff, Wales, UK; Sep. 13-16, 1999 ISSN: 0022-3573.

Database BIOSIS Online! Bioscience Information Service, Philadelphia, PA, US; 1992 Hayamizu K. et al., "Retroviral reverse transcriptase-inhibitory activity of flavonoid and tannin compounds", Database accession No. PREV199294037003 XP-002191773, abstract & Bulletin of The College of Agriculture & Veterinary Medicine Nihon, No. 49, 1992, pp. 35-41, 1992 ISSN: 0078-0839.

\* cited by examiner

METHOD FOR THE PRODUCTION OF PHYLLANTHUS EXTRACTS

This application is the U.S. National Stage of International Application No. PCT/EPO1/11526, filed Oct. 5, 2001.

The invention relates to a method for the production of an extract of *Phyllanthus* wherein (a) *Phyllanthus* components are extracted with an ethanol/water mixture of 5–85% m/m to which a heavy-metal chelator is added at a concentration of 0.001–3% m/m; (b) the primary extract obtained in step (a) is contacted and concentrated with (ba) Indian Sterculia gum at a final concentration of 0.5–5.0% mm relative to the sum of the extractive substances or (bb) one or more polymers and impendable and/or soluble substance(s); and (c) the concentrated extract obtained in step (b) is dried. The method according to the invention leads to particularly high yield of pharmaceutically effective plant ingredients and is thus of particular interest for therapeutic applications. In a preferred embodiment the method of the invention includes a filtration step of the primary extract. It is further preferred that a lipoid is added during the extraction process. The *Phyllanthus Phyllanthus amarus* is preferred. Moreover, the invention relates to pharmaceutical compositions containing the extracts obtained by the method of the invention.

The plant genus *Phyllanthus* belongs to the sub-family of the Phyllanthoideae which belongs to the family of the Euphorbiaceae. In total, the genus *Phyllanthus* comprises about 700 known varieties which come from tropical and subtropical areas in Australia, China, the Philippines, Thailand, Indonesia, Burma, India, East and West Africa and North America, Mexico, Cuba, the Caribbean and Venezuela. Only rarely are representative of this genus found in the Northern moderate zones.

Plants of the genus *Phyllanthus* contain secondary plant ingredients which, under the influence of light, temperature, oxygen and heavy-metals, are subject to oxidative degradation processes. In this respect, hydrolysable tanning agents are to be mentioned, such as the didehydrohexahydroxy-diphenol amariine or geraniine, a ellagitannin dominating in quantity. An additional group of ingredients (lignanes), the phyllanthines, is specific to the species *Phyllanthus amarus* Schumach et Thonn, whereby, primarily, phyllanthine and hypophyllanthine are to be mentioned; the former dominates in quantity. Phyllanthines and ellagitannins have in common their antioxidative reactivity, which characterises them, on the one hand, as important active agents and, on the other hand, as easily destructible. Whereas the ellagitannins are substances which are polar regarding their physico-chemistry and are very easily water-soluble, the phyllanthines preferably dissolve in organic solvents or mixtures of the latter with water. Both substance classes occur, alongside a series of ubiquitous primary and secondary plant ingredients, in aqueous preparations (Infuse/Decocte), as common in traditional folk medicine. In the case of the phyllanthines, this might be surprising to the non-skilled person in the art; for the person skilled in the art, however, this finding can be easily explained since plants contain miscellaneous solvent-mediating substance mixtures. With regard to the solving behavior of individual components, complex mixtures of several substances thus behave completely different, as the case may be, than would be expected for one ingredient alone. Both for the drug *Phyllanthus amarus* itself and for aqueous and alcoholic preparations (methanol, ethanol, butanol), there is a series of contradicting pharmacological data in vitro and in vivo. In particular, results of analyses regarding an antiviral activity range from strongly effective to non-effective. For a broad overview see Hager's Handbuch der pharmazeutischen Praxis, 5$^{th}$ edition, Vol. 3, Drogen L-Z, Springer Verlag, 342–343.

This situation is irritating at first sight only; a detailed analysis of the preparations used in the various analyses quickly leads to the result that the chosen preparations have differed drastically in essential substance-related features.

Due to this situation as to data, the mixtures of active gents cannot be compared, see M. H. Kreuter, Phytopharmaceutical Technology: Progress in Process Evaluation and Process Optimizing, Plenary Lecture, 46$^{th}$ Annual Congress of the Society for Medicinal Plant Research, Vienna, 1998. Based on the knowledge regarding the therapeutic efficacy by the evidence-based use of various ethnic groups, checking of the efficacy and safety of *Phyllanthus* by means of an application form which can be rationally handled clinically is desired.

However, the above arguments lead to a series of conditions for such a therapeutic agent which have to be fulfilled. From a pharmaco-dynamic and pharmaco-kinetic point of view, a high substance authenticity has to be respected with regard to the material of the archetypical application form. The process up to the formulation of the active agent must not lead to the formation of process-typical secondary products, which would consequently imply a material deviating from the ideal active agent.

Thus, it is known that, hydrolysable tanning agents forming complexes that are difficult to dissolve react with heavy-metals, hydrolise, oxydate and form non-soluble macromolecular precipitates. For an overview, see Schneider G., Pharmazeutische Biologie, 2., new and revised edition, Mannheim, Vienna, Zürich, Bibliographisches Institute, 1985, 307–308. Depending on the reaction conditions (temperature, time, oxygen), during the extraction process, this leads to a more or less intense loss of native ellagitannins. In contrast to the traditional fresh preparation of smallest amounts of infusions (tea), which can be taken within a time as short as possible, the large-scale technical production requires considerably more time. In this context, the result is an unproportionally higher entry of activation and maintenance energies for the process of the formation of secondary products, which is to be avoided. Thus, the classic aqueous and aqueous-alcoholic extraction of the *Phyllanthus* drug in large scale amounts leads to a drastic loss of ellagitannins and phyllanthines, due to the above influences.

Moreover, it is known that within the large scale technical production, large amounts of primary extraction liquid occur which are converted to a viscous extract (soft extract) by means of initially partially removing the extractive agent (destillation). This viscous extract is characterised by a comparably high content of solids (preferably 20–40% proportion of solids). During the classic carrying out of the method, this process step, too, leads to a massive loss of ellagitannins and phyllanthines. Due to the removal of the solving agent, sedimentations and flotations occur, since the solubility product of various ingredients is exceeded. Extractive agents fix to parts of the machines responsible for the transfer of heat (heat exchanger), stick to them and burn into them. Layers develop which cannot be protected from the cold of evaporation of the evaporating solving agent. In this way, the results are secondary products with an unknown activity, on the one hand, and loss of native agents, on the other hand.

The following characteristics are also not met in the methods known in the state of the art: The process has to be valid, must not exhibit any uncontrollable critical parameters and must lend itself to large-scale application. The active agent should be able to be formulated in a dry, solid aggregate condition and in a powder form. Pharmaceutically acceptable adjuvants by means of which this target can be achieved may be used. With regard to its chemical, biological and physical characteristics, the active agent has to be stable under suitable storage conditions. The active agent must lend itself to integration into a pharmaceutically acceptable drug formulation (preferably coated tablet, capsule, sugar-coated tablet). Thus, the technical problem of the invention was to provide a method which solves the problems discussed above.

The solution to said technical problem is achieved by providing the embodiments characterized in the claims.

Thus, the present invention relates to a method for the production of an extract of *Phyllanthus* wherein (a) *Phyllanthus* components are extracted with an ethanol/water mixture of 5–85% m/m to which a heavy-metal chelator is added at a concentration of 0.001–3% m/m; (b) the primary extract obtained in step (a) is contacted and concentrated with (ba) Indian Sterculia gum at a final concentration of 0.5–5.0% mm relative to the sum of the extractive substances or (bb) one or more polymers and impendable and/or soluble substance(s); and (c) the concentrated extract obtained in step (b) is dried.

The term "*Phyllanthus* components", as used according to the invention, comprises all the components of a whole plant, such as e.g. leaves, bark, blossoms, stalk, seeds, fruit, branches, stems, roots, wood, as well as parts thereof. These *Phyllanthus* components may exhibit the same, similar or non-related ingredients. In the method according to the invention, different *Phyllanthus* components can be used individually or together and different *Phyllanthus* components of different *Phyllanthus* varieties can be used individually or combined together. "Several" *Phyllanthus* components refers to the whole of *Phyllanthus* components, for example in the form of whole plants. In the method according to the invention, the *Phyllanthus* components can be used after pre-treatment or without pre-treatment. Pre-treatment comprises, for example, processes such as drying, for example of leaves.

Due to the introduction of new method steps in the preparation of *Phyllanthus* and by the new combination of method steps, the invention, for the first time, provides a method which, during large-scale technical application, provides reproducible and valid plant extracts in which pharmacologically effective plant components are essentially maintained in active form. Thus, in the invention, it was surprisingly found that the above discussed polymerisation to insoluble macromolecules and the undesired loss of pharmaceutically active ellagitannins and phyllanthines connected therewith can be prevented effectively by the addition of heavy-metal chelators to the extractive agent.

The above discussed exceeding of the solubility product both of polar and apolar substances can clearly be delayed in the early phases of the extract thickening, if a solving agent mixture of average polarity is chosen. For this reason, in the present invention, an ethanol/water mixture of preferably 35–45% m/m is used. This measure, however, does not suffice and prevents the process of the formation of secondary products only in an insufficient manner. Surprisingly, by means of adding Indian Sterculia gum, both the sedimentation and the flotation of extractive agents can be prevented effectively during the whole concentration phase. As surprisingly found, this phenomenon is due to the polymer's characteristic, on the one hand, to still swell homogeneously in 45% m/methanol and, on the other hand, to be inert against the ellagitannins. Due to these characteristics, it is possible to obtain large-scale amounts of viscous extract without the discussed critical phase separations occurring. True that pharmaceutically acceptable alternative polymers such as, for example, polyvinylpyrrolidone or hydroxypropyl, ethyl and methyl celluloses dissolve in 45% m/methanol but they lead to precipitations with ellagitannins; polymers of the type of the *Gummia arabicum* or Traganth cannot be hydrated and are out of the question as resinous gums.

In a preferred embodiment of the invention, in step (a), an ethanol/water mixture of 35–45% m/m is used for the extraction.

35–45% m/methanol is preferred, since, with sufficient lipophilia for optimum extraction, it allows the direct protection entry of the Sterculia gum.

In another preferred embodiment, in step (a), the heavy-metal chelator is added at a concentration of 0.1–1.0% m/m.

In another preferred embodiment, in step (ba), Indian Sterculia gum is added to the primary extract at a final concentration of 0.7–1.3% m/m.

Moreover, in another preferred embodiment, in step (bb), the substance(s) is/are a pharmaceutically acceptable polysaccharide/pharmaceutically acceptable polysaccharides at a final concentration of 2–50 m/m relative to the sum of the extractive agents.

In a particularly preferred embodiment, the final concentration of the polysaccharide(s) ranges from 1–10% m/m.

In a preferred embodiment, after step (a) and before step (b) (a) a filtration with the primary extract obtained in step (a) is carried out, wherein the filter has an exclusion volume of 0.05–0.5 μm.

As a natural product, *Phyllanthus amarus* contains, more or less frequent and at a more or less intense concentration, bacterial endorsers, fungus spores which, even during an extraction containing alcohol, are not killed in a reliable manner. Since it is known that a series of ingredients of *Phyllanthus amarus* are thermolabile, thermal methods the intensity of which would suffice to kill these spores, is out of the question for removing these contaminants. Surprisingly, it was found that the extraction liquid obtainable according to the first method step above, can be filtrated without (or nearly without) loss of substance, preferably ultra-filtrated, when multi-base acids, or the salts thereof, preferably disodiumhydrogen citrate, are added, wherein the pore size is chosen in a way that makes an escape of the spores due to their size impossible. Without the addition of the above agent, during the process of filtration, polymerisation processes occur which lead to coarse-flaky precipitations on the filtrate or retentate side and, apart from an obvious formation of secondary products, block the pores of the device and bring the filtration process to a halt.

In a particularly preferred embodiment, the filter has an exclusion volume of 0.10.3 μm.

In another particularly preferred embodiment, the filtration is an ultra-filtration.

In another particularly preferred embodiment, a lipoid at the final concentration of 1–100% m/m relative to the extractive agents is added in step (a) or before step (b).

Due to the addition of lipoids before the filtration, contaminations at lipophilic organic contaminations (for example dioxins, aflatoxines, organochloric pesticides or polychloric biphenyls) are accumulated and, in this way, removed from the extraction liquid. Due to the droplet size of the charged lipoids, these are retained like the spores, too, in the retentate and a highly pure solution of active agents is obtained on the filtrate side.

Much particularly preferred, the lipoid is selected from the group of plant oils, waxes and fatty acids.

In a preferred embodiment, the heavy-metal chelator is a multi-base organic acid or the salt thereof.

In a particularly preferred embodiment, the heavy-metal chelator is the multi-base organic acid disodiumhydrogen citrate.

In a particularly preferred embodiment, one or more pharmaceutically acceptable adjuvant(s) are added to the concentrated extract obtained in step (b) before the drying.

Pharmaceutically acceptable adjuvants include pharmaceutically acceptable carriers and pharmaceutically acceptable diluting agents. Preferred examples of such adjuvants are maltodextrin and highly-dispersed silicon dioxide.

Further examples of suitable carriers are known to the person skilled in the art and are monographed as pharmaceutical adjuvants in international pharmaceutical books.

In another preferred embodiment, the drying in step (c) is carried out in the presence of one or more pharmaceutically acceptable adjuvant(s).

Furthermore, the present invention relates to a method for the production of a pharmaceutical preparation, a food supplement or a medicinal product, wherein the steps of the methods according to the invention are carried out and wherein the dried extract obtained in step (c) is formulated with one or more pharmaceutically acceptable adjuvant(s).

The pharmaceutical preparations can be administered to an individual in a suitable dosage. An administration can be carried out orally or parenterally, e.g. in a intravenous, intraperitoneal, subcutane, perinodale, intramuscular, topic, intradermal, intranasal, oral or intrabronchial way or via a catheter at a site in an artery. The amount of the dosage is determined by the doctor giving treatment and essentially depends on clinical factors. These factors are known in the field of medicine and science and comprise, for example, the height and the weight, the body surface, the age, the sex and the general condition of the patient, the specific composition to be administered, the period of treatment, the type of administration and the simultaneous treatment, if any, with other pharmaceutical preparations. A typical dose can, for example, range from 0.001 to 5000 mg extractive substances, wherein doses below or above this range of the example, especially in consideration of the factors mentioned above, are possible. In general, in the case of regular administration of the composition according to the invention, the dose should be within a range of 100 mg and 1000 mg units per day. If the composition is administered intravenously, which is not recommended preferably in order to minimise the danger of an anaphylactic reaction, the dose should be in a range from 1 µg and 10 mg units per kilogram bodyweight per minute.

The present invention further relates to a method for the production of a pharmaceutical preparation, a food supplement or a medicinal product, wherein the steps according to the invention are carried out and wherein the drying in step (c) is carried out in the presence of one or more pharmaceutically acceptable adjuvant(s).

Furthermore, the present invention relates to a method for the production of a pharmaceutical preparation, a food supplement or a medicinal product, wherein the steps of the methods according to the invention are carried out and wherein the pharmaceutically acceptable adjuvant(s) is (are) added before the drying in step (c).

In a preferred embodiment, the adjuvants are maltodextrin and/or high-disperse silicon dioxide.

In a further preferred embodiment, the drying takes place by means of spray, band or freeze drying.

In addition, in a preferred embodiment, the *Phyllanthus* is *Phyllanthus amarus*.

In a particularly preferred embodiment, the *Phyllanthus amarus* is the *Phyllanthus amarus* Schumach et Thonn.

Furthermore, the present invention relates to a *Phyllanthus* extract obtainable according to the method of the invention.

Moreover, the present invention also relates to a pharmaceutical preparation obtainable according to the method of the invention.

In addition, the present invention relates to a pharmaceutical preparation containing a *Phyllanthus* extract produced according to the method of the invention.

In a preferred embodiment, the form of administration is a tablet, a sugar-coated tablet, a hard gelatine capsule or a soft gelatine capsule.

In a particularly preferred embodiment, the tablet is a coated tablet.

The Examples illustrate the invention.

EXAMPLE 1

Extraction of *Phyllanthus amarus* Leaves

Dried *Phyllanthus amarus* leaves were filled into an extraction device (steel vessel). 50% v/v EtOH was used as an extraction agent. Furthermore, disodiumhydrogen citrate at a final concentration of 0.1–1.0% m/m was added to the solution. The EtOH content was checked by measuring the density and corresponded to 35–45% m/m. The ratio of drug to solvent was 1:10 (+/−3 solvent). The leaves were extracted for 1 hour at a temperature of between 30 and 50° C. Then, the miscela was washed with water over a filter (corresponds to three parts drugs) and pressed. Then, the mixture was filtered through a membrane having an exclusion volume of between 0.1 to 0.3 µm. Indian Sterculia gum, which had been dissolved in ethanol/water or in absolute ethanol before, was added to the solution. The mixture was then concentrated by means of evaporation under reduced pressure (about 300 mB lowered to 20 mB), a temperature of 30–60° C. (+/−5° C.) being used, until the material had a dry content of 20 to 40% (m/m). Subsequently, the soft extract was mixed with maltodextrin until a homogeneous suspension was obtained. Then, the mixture was subjected to spray drying.

The values of the pesticides analysed herein are shown in Table 1, the ellagitannin values are shown in Table 2.

EXAMPLE 2

Extraction of *Phyllanthus amarus* Leaves

The method was carried out according to Example 1 with the following modifications: After maltodextrin was added, the mixture was placed in a short-time heater at a temperature of 100° C. for 36 seconds. Thus, the microbial contamination of the drug was reduced. The mixture was dried until the water content was below 5%. During the drying process, the temperature at the outlet of the heating unit did not exceed 90° C. (+/−5%). Silica was added during and after the drying process.

The dried product was mixed and then sieved.

The values of the pesticides analysed herein are shown in Table 1, the ellagitannin values are shown in Table 2.

It can be seen from Table 2 that the ellagitannin values are not substantially changed by the short-time heating.

EXAMPLE 3

Extraction of *Phyllanthus amarus* Leaves

The method was carried out according to Example 1 with the following modifications:

Prior to the filtration, a lipid (miglyol) was added to the mixture (final concentration of 54.9% m/m relative to the extractive agents). Then, the mixture was filtered through a membrane having an exclusion volume of between 0.1 and 0–3 µm. Due to the previous addition of lipid, the contaminations of lipophilic organic contaminations are removed during the ultra filtration. The subsequent concentration, mixing and spray drying have been described in Example 1.

The values of the pesticides analysed herein are shown in Table 1, the ellagitannin values are shown in Table 2.

It can be seen from Table 1 that, compared to Examples 1 and 2, there is a significant purification of the undesired lipophilic contaminations and/or residues below the detection limit.

Table 2 shows clearly that the ellagitannins are not removed.

TABLE 1

| | Pesticide value in the end product (in ppm) | | | detection limit (in ppm) |
|---|---|---|---|---|
| | Example 1 | Example 2 | Example 3 | |
| α-endosulfane | n.d. | 0.01 | n.d. | 0.01 |
| β-endosulfane | <0.01 | 0.01 | n.d. | 0.01 |
| endosulfane sulphate | <0.02 | 0.02 | n.d. | 0.02 |
| α-HCH | <0.005 | 0.006 | n.d. | 0.005 |
| lindane (γ-HCH) | 0.018 | 0.016 | n.d. | 0.005 | n.d.: not detectable

TABLE 2

| | Values in the end product (in %) | | |
|---|---|---|---|
| | Example 1 | Example 2 | Example 3 |
| ellagitannins | 11.44 | 10.69 | 12.65 |

The invention claimed is:

1. A method for the production of an extract of *Phyllanthus* comprising:
   (a) extracting *Phyllanthus amarus* components with an ethanol/water mixture of 5–85% m/m to which a heavy-metal chelator is added at a concentration of 0.001–3% m/m;
   (b) contacting and concentrating the primary extract obtained in step (a) is with
      (ba) Indian Sterculia gum at a final concentration of 0.5–5.0% m/m relative to the sum of the extractive substances or
      (bb) one or more polymers and impendable and/or soluble substance(s); and
   (c) drying the concentrated extract obtained in step (b).

2. The method according to claim 1, wherein in step (a) an ethanol/water mixture of 35–45% m/m is added for the extraction.

3. The method according to claim 1, wherein in step (a) the heavy-metal chelator is added at a concentration of 0.1–1.0% m/m.

4. The method according to 1, wherein in step (ba) Indian Sterculia gum at a final concentration of 0.7–1.3% m/m is added to the primary extract.

5. The method according claim 1, wherein in step (bb) the substance(s) is/are a pharmaceutically acceptable polysaccharide/pharmaceutically acceptable polysaccharides at a final concentration of 2–50% m/m relative to the sum of the extractive agents.

6. The method according to claim 5, wherein the final concentration of the polysaccharide(s) is in the range of 1–10% m/m.

7. The method according claim 1, wherein after step (a) and before step (b)
   a filtration is carried out with the primary extract obtained in step (a), wherein the filter has an exclusion volume of 0.05–0.5 µm.

8. The method according to claim 7, wherein the filter has an exclusion volume of 0.1–0.3 µm.

9. The method according to claim 7, wherein the filtration is an ultra-filtration.

10. The method according claim 7, wherein in step (a) or before step (b) a lipid is added at a final concentration of 1–100% m/m relative to the extractive agents.

11. The method according to claim 10, wherein the lipoid is selected from the group consisting of plant oils, waxes, fatty acids, and any combinations thereof.

12. The method according claim 1, wherein the heavy-metal chelator is a multi-base organic acid or the salt thereof.

13. The method according to claim 12, wherein the multi-base organic acid is disodiumhydrogen citrate.

14. The method according to claim 1, wherein one or more pharmaceutically acceptable adjuvant(s) are added to the concentrated extract obtained in step (b) before the drying.

15. The method according to claim 14, wherein the adjuvants are maltodextrin and/or high-disperse silicon dioxide.

16. The method according to claim 1, wherein the drying in step (c) is carried out in the presence of one or more pharmaceutically acceptable adjuvant(s).

17. The method according to claim 1, wherein the pharmaceutically acceptable adjuvant(s) are added before the drying in step (c).

18. The method according to claim 1, wherein the drying is carried out by means of spray, band or freeze drying.

19. The method according to claim 1, wherein the *Phyllanthus amarus* is the *Phyllanthus amarus* Schumach et Thonn.

20. A method for the production of a pharmaceutical preparation, a food supplement or a medicinal product, wherein the steps of the methods comprise:
   (a) extracting *Phyllanthus amarus* components with an ethanol/water mixture of 5–85% m/m to which a heavy-metal chelator is added at a concentration of 0.001–3% m/m;
   (b) contacting and concentrating the primary extract obtained in step (a) with
      (ba) Indian Sterculia gum at a final concentration of 0.5–5.0% m/m relative to the sum of the extractive substances or
      (bb) one or more polymers and impendable and/or soluble substance(s); and
   (c) drying the concentrated extract obtained in step (b)
   and wherein the dried extract obtained in step (c) is formulated with one or more pharmaceutically acceptable adjuvant(s).

21. The method wherein the drying in step (c) is carried out with one or more pharmaceutically acceptable adjuvant (s).

22. The method according to claim 20, wherein the adjuvants are maltodextrin and/or high-disperse silicon dioxide.

23. The method according to claim 20, wherein the drying is carried out by means of spray, band or freeze drying.

24. A *Phyllanthus* extract prepared by:
   (a) extracting *Phyllanthus amarus* components with an ethanol/water mixture of 5–85% m/m to which a heavy-metal chelator is added at a concentration of 0.00 1–3% m/m;
   (b) contacting and concentrating the primary extract obtained in step (a) with
      (ba) Indian Sterculia gum at a final concentration of 0.5–5.0% m/m relative to the sum of the extractive substances or
      (bb) one or more polymers and impendable and/or soluble substance(s); and
   c) dryinig the concentrated extract obtained in step (b).

25. An extract according to claim 24, wherein the extract is in the form of a pharmaceutical preparation.

26. An extract according to claim 24, wherein the pharmaceutical preparation comprises a tablet, a sugar-coated tablet, a hard gelatine capsule or a soft gelatine capsule.

27. An extract according to claim 26, wherein the tablet comprises a coated tablet.

* * * * *